(12) United States Patent
Teeslink et al.

(10) Patent No.: US 9,254,145 B2
(45) Date of Patent: Feb. 9, 2016

(54) ATHERECTOMY DEVICE

(75) Inventors: Charles Teeslink, Chattanooga, TN (US); Dirk Hoyns, Chattanooga, TN (US)

(73) Assignee: ADVANCED CATHETER THERAPIES, INC., Chattanooga, TN (US)

(*) Notice: Subject to any disclaimer, the term of this patent is extended or adjusted under 35 U.S.C. 154(b) by 678 days.

(21) Appl. No.: 13/583,838

(22) PCT Filed: Mar. 11, 2011

(86) PCT No.: PCT/US2011/028075
§ 371 (c)(1),
(2), (4) Date: Nov. 15, 2012

(87) PCT Pub. No.: WO2011/112918
PCT Pub. Date: Sep. 15, 2011

(65) Prior Publication Data
US 2013/0060270 A1 Mar. 7, 2013

Related U.S. Application Data

(60) Provisional application No. 61/312,846, filed on Mar. 11, 2010.

(51) Int. Cl.
*A61B 17/22* (2006.01)
*A61B 17/3207* (2006.01)
*A61B 17/32* (2006.01)

(52) U.S. Cl.
CPC . *A61B 17/320783* (2013.01); *A61B 17/320758* (2013.01); *A61B 2017/22079* (2013.01); *A61B 2017/320008* (2013.01); *A61B 2017/320766* (2013.01); *A61B 2017/320791* (2013.01)

(58) Field of Classification Search
CPC ............. A61B 17/3207; A61B 17/320783; A61B 2017/320791; A61B 17/320758; B24B 5/485; H02K 7/06; F16H 25/12; F16H 25/20; F16H 25/2025; F16H 25/2059; F16H 37/12; F16H 27/124; F16H 37/16; F16H 37/124
USPC ............. 606/159; 604/22; 451/168, 462, 529; 310/20, 80, 12.14; 74/89.23, 424.83, 74/56, 57
See application file for complete search history.

(56) References Cited

U.S. PATENT DOCUMENTS 2,441,596 A * 5/1948 Reitter .............................. 74/57
3,672,587 A * 6/1972 Pierce ........................ 242/483.5
(Continued)

FOREIGN PATENT DOCUMENTS

JP 06030943 A 2/1994
WO 2008060277 A2 5/2008
(Continued)

OTHER PUBLICATIONS

International Search Report for PCT/US2011/028075 Mailed Nov. 22, 2011.

*Primary Examiner* — Todd E Manahan
*Assistant Examiner* — Charles Wei
(74) *Attorney, Agent, or Firm* — Miles & Stockbridge PC

(57) ABSTRACT

A device for modifying a body lumen of a mammal in need thereof is provided, comprising a helically-cut tube comprising cutting teeth, said helically-cut tube substantially coaxial with the longitudinal axis of said device, a ramp wire that is displaced from the longitudinal axis of said device over at least a portion of said ramp wire and is enclosed by said helically-cut tube over at least a part of the length of said ramp wire, a drive rod wherein the broach may be moved proximally, distally, and/or radially via proximal, distal, and radial motions, respectively, of the drive rod. Also provided are methods for using the device.

12 Claims, 11 Drawing Sheets

(56) References Cited

U.S. PATENT DOCUMENTS

| | | | |
|---|---|---|---|
| 3,768,745 A * | 10/1973 | Koller | 242/483.5 |
| 3,779,094 A * | 12/1973 | La Barre | 74/25 |
| 3,952,604 A * | 4/1976 | Baudler | 74/57 |
| 4,022,076 A * | 5/1977 | Metz | 74/441 |
| 4,031,765 A * | 6/1977 | Metz | 74/57 |
| 4,040,682 A * | 8/1977 | Poulsen | 74/25 |
| 4,343,200 A * | 8/1982 | Alworth et al. | 74/57 |
| 4,646,736 A | 3/1987 | Auth | |
| 4,728,319 A * | 3/1988 | Masch | 604/22 |
| 4,850,957 A | 7/1989 | Summers | |
| 4,883,460 A | 11/1989 | Zanetti | |
| 5,030,201 A | 7/1991 | Palestrant | |
| 5,074,841 A | 12/1991 | Ademovic | |
| 5,108,411 A | 4/1992 | McKenzie | |
| 5,116,352 A | 5/1992 | Schnepp-Pesch et al. | |
| 5,181,920 A | 1/1993 | Meuller et al. | |
| 5,195,954 A | 3/1993 | Schnepp-Pesch et al. | |
| 5,226,909 A | 7/1993 | Evans et al. | |
| 5,242,460 A | 9/1993 | Klein et al. | |
| 5,312,425 A | 5/1994 | Evans et al. | |
| 5,360,432 A * | 11/1994 | Shturman | 606/159 |
| 5,366,464 A | 11/1994 | Belknap | |
| 5,403,334 A | 4/1995 | Evans et al. | |
| 5,417,703 A | 5/1995 | Brown et al. | |
| 5,507,795 A | 4/1996 | Chiang et al. | |
| 5,540,113 A * | 7/1996 | Takei | 74/89.3 |
| 5,554,163 A * | 9/1996 | Shturman | 606/159 |
| 5,569,277 A | 10/1996 | Evans et al. | |
| 5,665,098 A | 9/1997 | Kelly et al. | |
| 5,695,507 A | 12/1997 | Auth et al. | |
| 5,709,698 A | 1/1998 | Adams et al. | |
| 5,746,758 A | 5/1998 | Nordgren et al. | |
| 5,876,414 A | 3/1999 | Straub | |
| 5,882,329 A | 3/1999 | Patterson et al. | |
| 5,895,397 A | 4/1999 | Jang et al. | |
| 5,895,398 A | 4/1999 | Wensel et al. | |
| 5,895,400 A | 4/1999 | Abela | |
| 5,895,402 A | 4/1999 | Hundertmark et al. | |
| 5,902,263 A | 5/1999 | Patterson et al. | |
| 5,928,186 A | 7/1999 | Homsma et al. | |
| 5,954,737 A | 9/1999 | Lee | |
| 6,001,112 A | 12/1999 | Taylor | |
| 6,036,708 A | 3/2000 | Sciver | |
| 6,206,900 B1 | 3/2001 | Tabatabaei et al. | |
| 6,242,667 B1 | 6/2001 | Bujard et al. | |
| 6,264,667 B1 | 7/2001 | McGuckin, Jr. | |
| 6,319,242 B1 * | 11/2001 | Patterson et al. | 604/508 |
| 6,322,572 B1 | 11/2001 | Lee | |
| 6,412,721 B2 * | 7/2002 | Kawabe et al. | 242/278 |
| 6,436,112 B2 | 8/2002 | Wensel et al. | |
| 6,447,525 B2 | 9/2002 | Follmer et al. | |
| 6,485,497 B2 | 11/2002 | Wensel et al. | |
| 6,530,935 B2 | 3/2003 | Wensel et al. | |
| 6,629,953 B1 | 10/2003 | Boyd | |
| 6,638,233 B2 | 10/2003 | Corvi et al. | |
| 6,692,508 B2 | 2/2004 | Wensel et al. | |
| 6,692,509 B2 | 2/2004 | Wensel et al. | |
| 6,945,977 B2 | 9/2005 | Demarais et al. | |
| 7,029,483 B2 | 4/2006 | Schwartz | |
| 7,172,610 B2 | 2/2007 | Heitzmann et al. | |
| 7,291,158 B2 | 11/2007 | Crow et al. | |
| 7,303,572 B2 | 12/2007 | Melsheimer et al. | |
| 7,316,697 B2 | 1/2008 | Shiber | |
| 7,329,267 B2 | 2/2008 | Weber | |
| 7,666,161 B2 * | 2/2010 | Nash et al. | 604/22 |
| 2003/0216760 A1 * | 11/2003 | Welch et al. | 606/159 |
| 2004/0133148 A1 | 7/2004 | Jacques | |
| 2008/0097499 A1 * | 4/2008 | Nash et al. | 606/159 |
| 2009/0048533 A1 * | 2/2009 | Miller | 600/567 |
| 2009/0105736 A1 | 4/2009 | Prudnikov et al. | |
| 2009/0149877 A1 * | 6/2009 | Hanson et al. | 606/159 |
| 2010/0187346 A1 * | 7/2010 | Ochiai et al. | 242/242 |

FOREIGN PATENT DOCUMENTS

| | | |
|---|---|---|
| WO | 2010002507 A1 | 1/2010 |
| WO | 2010002549 A2 | 1/2010 |

* cited by examiner

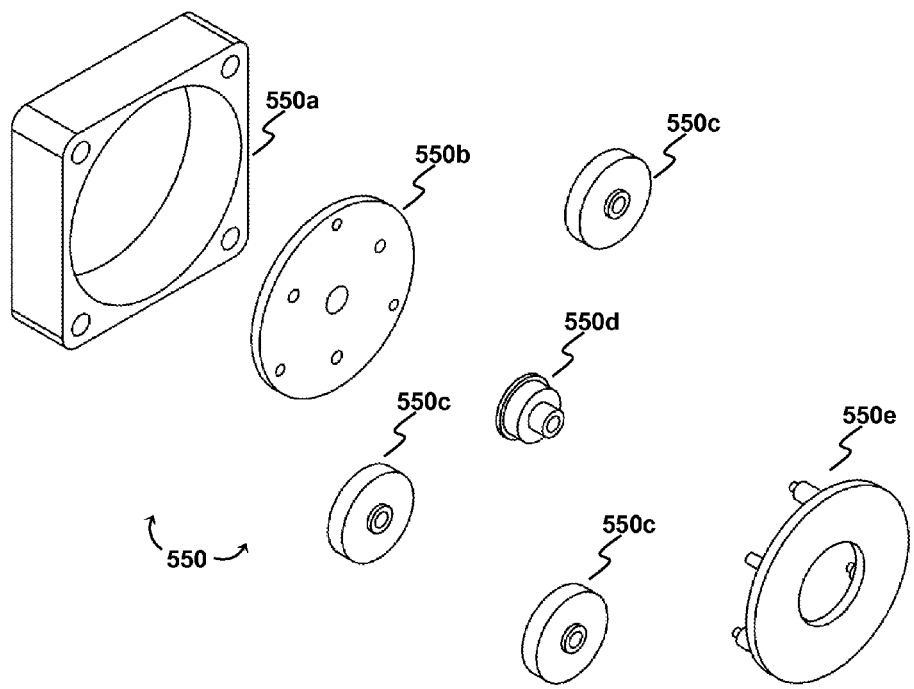
FIG. 12A
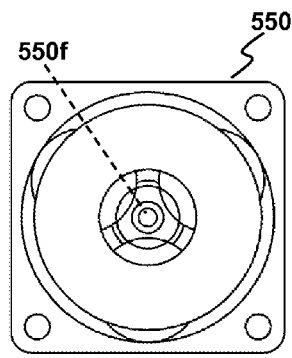
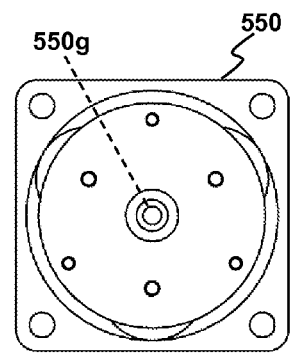
FIG. 12B  FIG 12C

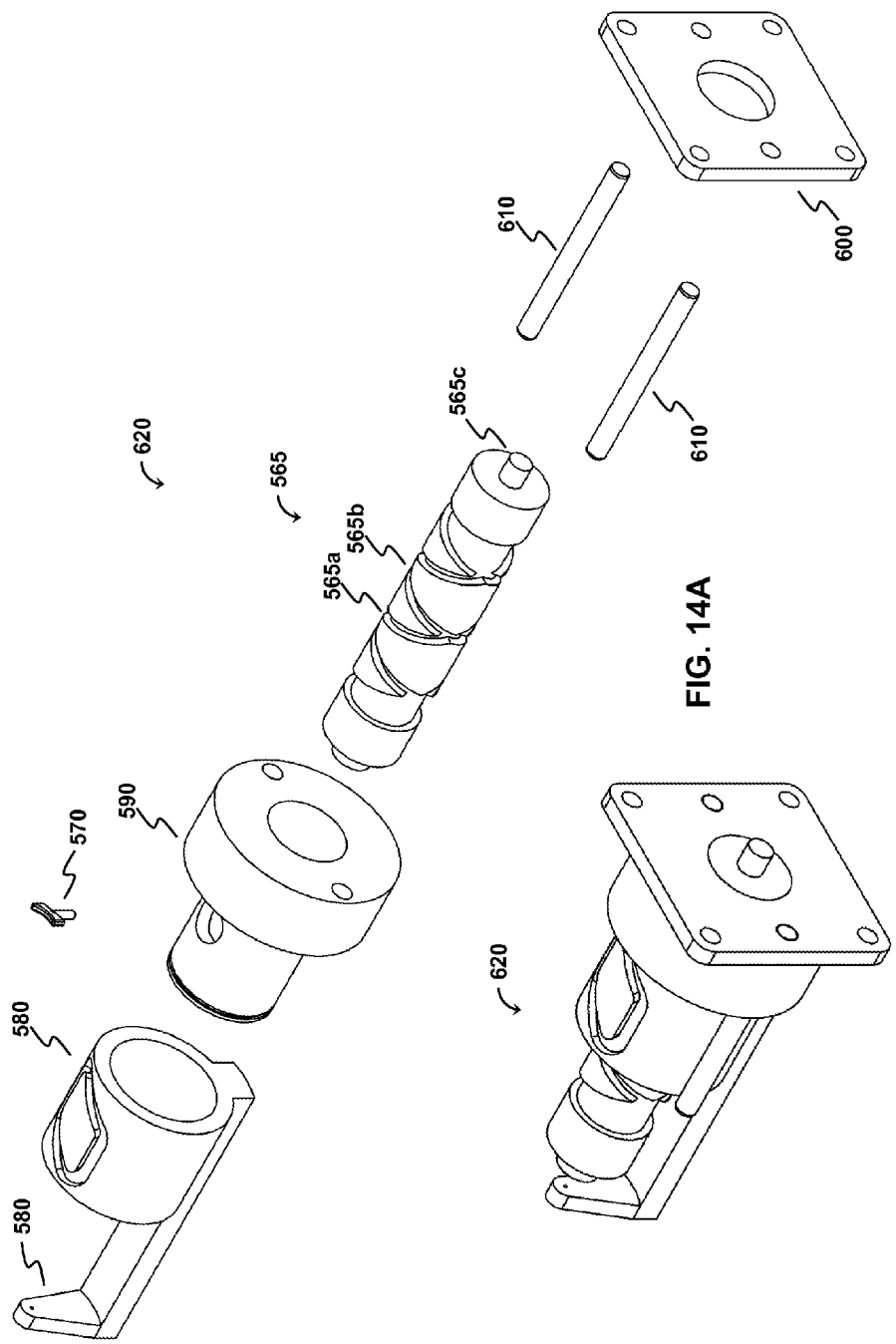

ATHERECTOMY DEVICE

BACKGROUND

1. Field of the Instant Disclosure

The present application relates generally to a catheter device and methods for the removal of atherosclerotic plaques in medical procedures. More particularly, the disclosure relates to a catheter device comprising multiple cutting surfaces which cut, rotate, reciprocate, and rotate again.

2. Description of Related Art

Many devices for minimally invasive removal of plaque and blockages from a body lumen (i.e., for atherectomy) exist. Such devices may be used in, for example, coronary arteries to restore circulation. Contrary to angioplasty and stenting, which only push blockages/plaques into the inner wall of the lumen, atherectomy involves introducing a catheter comprising scraping or cutting means into the lumen. Operation of the scraping or cutting means works to remove the blockages/plaques, thereby restoring circulation through the lumen. This procedure is also distinguished from endarterectomy, which comprises the surgical removal of plaque from the inner wall of a diseased artery, along with portions of the arterial lining, leaving a smooth tunica externa (the outermost layer of the blood vessel).

Devices of the prior art rely upon multiple insertions and removals of said devices over a guide-wire to enable adequate plaque removal and opening of the lumen. Continued removal and reintroduction dramatically increases the possibility of procedural complications and adds significant time to the procedure.

The technical problem underlying the present disclosure was therefore to overcome these prior art difficulties by creating a device that would successfully remove plaques/blockages without requiring multiple insertions and reintroductions. The solution to this technical problem is provided by the embodiments characterized in the claims.

BRIEF SUMMARY

The present application discloses an improved endovascular plaque excision system intended to replace and/or provide adjunctive therapy to balloon angioplasty by mechanically and continuously removing plaque from arteries or other body lumens.

The present application provides a device comprising a catheter section, a drive/pump hand piece, and fluid ingress and egress connections that move a series of increasing height cutting teeth that pass up, travel axially, and then retract through an aperture located toward the distal end of the catheter section (the treatment section).

The present application provides a device comprising cutter teeth connected to a helically-cut tubular member that has a constrained length defined by a drive rod that allows it to move as a section and prevents the helically-cut tube from collapsing or over-expanding on a ramp wire on which the helically-cut tube runs when under tension.

The ramp wire is anchored in the distal tip of the catheter, and provides the predetermined path the cutter teeth follow as they advance up, axially along and down through the aperture in the catheter treatment section.

In one embodiment, the present disclosure provides a device substantially as shown and described.

In one embodiment, the present disclosure provides a method for removing plaque from a body lumen of a mammal in need thereof, substantially as shown and described.

In one embodiment, the present disclosure provides a device comprising: a longitudinal axis; a broach comprising cutting teeth, said broach substantially coaxial with the longitudinal axis; a ramp wire substantially coaxial with the longitudinal axis, wherein a portion of said ramp wire deviates from said longitudinal axis; a drive rod substantially coaxial with the longitudinal axis; and wherein the ramp wire is slidably enclosed by the broach, wherein the broach is moved proximally, distally, and radially via the drive rod.

BRIEF DESCRIPTION OF THE DRAWINGS

For a further understanding of the nature, objects, and advantages of the present disclosure, reference should be had to the following detailed description, read in conjunction with the following drawings, wherein like reference numerals denote like elements.

FIG. 7A shows the teeth in the "home" position; FIG. 7B shows the cutter teeth advancing up the stationary ramp wire and traveling through the window to cut plaque. FIG. 7C shows the cutter teeth retracting down the ramp wire at the end of a stroke, at which point plaque may be flushed from the teeth. FIG. 7C also shows clearly the displacement of the ramp wire with respect to the longitudinal axis of the device, over which displacement the broach travels. Figures of the "(1)" series, e.g., 7A(1), show the device as it would appear during operation; figures of the "(2) series, e.g., 7A(2), show the device as it would appear with the distal end of the cylinder cut away.

FIG. 8A shows the teeth rotated about the longitudinal axis, about 90 degrees and up to 180 degrees in preparation for return to "home" position; FIG. 8B shows the cutter teeth advancing up the ramp wire and traveling through the window to return to the "home" position. As shown in FIGS. 8B(1) and 8B(2), while the teeth are in the window region of the device, rotation of the broach about the longitudinal axis has caused them to be occluded by the cylinder at this stage (compare with FIGS. 7B(1) and 7B(2)). FIG. 8C shows the cutter teeth at the end of the ramp wire at the end of a stroke, at which point the teeth may be rotated again to the position shown in FIGS. 7A(1) and (2). Figures of the "(1)" series, e.g., 8A(1), show the device as it would appear during operation; figures of the "(2) series, e.g., 8A(2), show the device as it would appear with the distal end of the cylinder cut away.

FIG. 12 shows the planetary gear packs. FIG. 12A is an exploded view of a planetary gear pack; FIG. 12B shows the drive input of a planetary gear pack; FIG. 12C shows the drive output of a planetary gear pack.

FIG. 13 shows the peristaltic pump assembly.

FIG. 14 shows the cutter drive assembly. FIG. 14A is an exploded view of the cutter drive assembly, and FIG. 14B shows the assembled cutter drive assembly.

DETAILED DESCRIPTION

Before the subject catheter is further described, it is to be understood that the disclosure is not limited to the particular embodiments of the disclosure described below, as variations of the particular embodiments may be made and still fall within the scope of the appended claims. It is also to be understood that the terminology employed is for the purpose of describing particular embodiments, and is not intended to be limiting. Instead, the scope of the present disclosure will be established by the appended claims.

In this specification and the appended claims, the singular forms "a," "an," and "the" include plural reference unless the context clearly dictates otherwise. Unless defined otherwise, all technical and scientific terms used herein have the same meaning as commonly understood to one of ordinary skill in the art to which this disclosure belongs.

In one embodiment, the disclosed device (1) offers continuous plaque removal from a single catheter insertion over a guide wire, for any given lesion. The guide wire may be, for example, for example, 0.018". This functionality alone differentiates the instant device from those of the prior art, which require multiple removal and reintroductions over a guide wire to facilitate adequate plaque removal and subsequent opening of the lumen. The continued removal and reintroduction over the guide wire required by the prior art devices increases the possibility of procedural complications and adds significant time to the overall procedure.

The instant device (1) comprises a longitudinal axis (X), and is intended to have a 5 Fr. crossing profile, although persons having ordinary skill in the relevant arts will understand that other sizes are contemplated, thereby allowing for maximum utilization in the lower extremities (e.g., for limb salvage related to diabetes or other causes of inadequate leg circulation, for coronary use, or for use in the carotid arteries). Of course, the intended crossing profile does not limit the device to limb salvage cases, but simply provides a target size that could be useful in other areas of the anatomy that could benefit from this next-generation technology.

Figure 1:
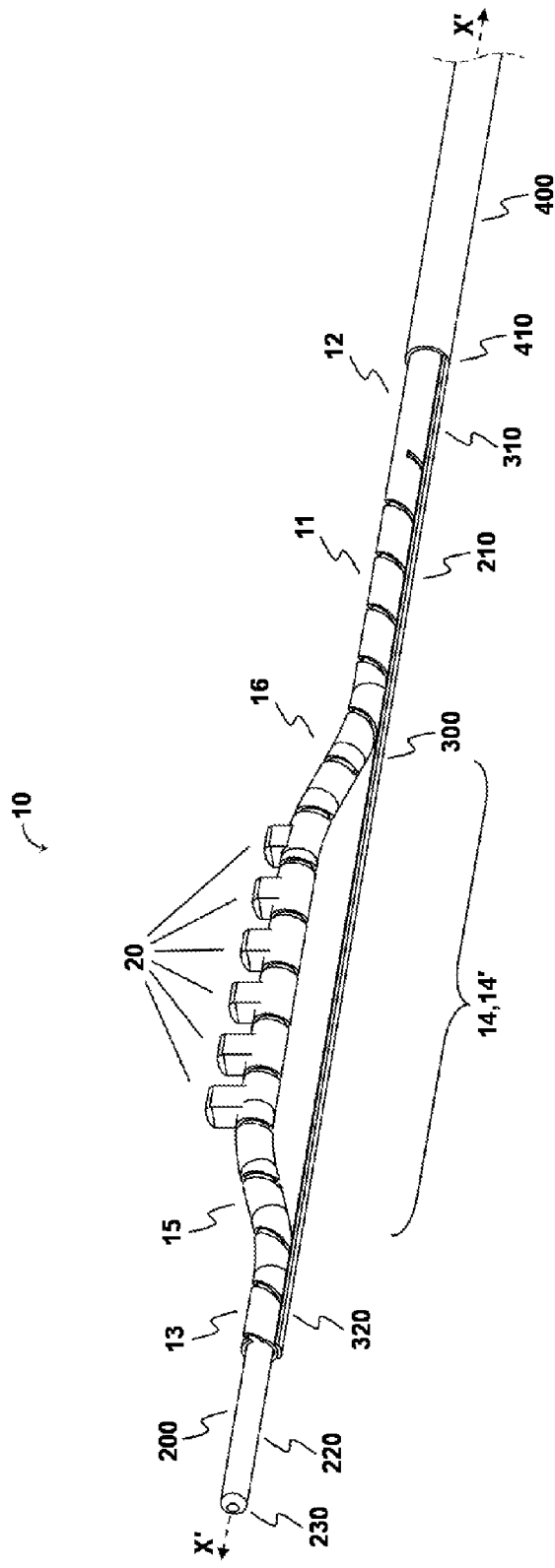
FIG. 1 shows the broach (including teeth), ramp wire, drive rod, and drive tube of a device of the present disclosure.

Referring to FIG. 1, the instant device (1) comprises a broach (10), wherein the broach may comprise a series of progressively taller cutting surfaces (20), or "teeth" mounted on a single, continuous surface. The teeth (20) toward the distal end of the device (1) are progressively taller than the teeth (20) toward the proximal end of the device (1). Optionally, the teeth (20) may be of the same height with respect to one another. Broaches are shaped similarly to a saw, except that the height of the cutting surfaces (teeth) increases in one direction along the long axis (the length) of the tool. Broaches are used typically to remove excess material from metal or wood—a process called "broaching"—and are particularly useful for creating or enlarging circular and non-circular holes, splines, and flat surfaces.

As shown in FIG. 1, the broach (10) comprises a helically-cut metal tube (11), a longitudinal axis (X'), proximal and distal ends (12 & 13, respectively), and a length therebetween. The broach further comprises cutting surfaces (20), or "teeth" or "chisels" that are attached to (or formed from a portion of) said helically-cut metal tube (11). The teeth (20) project substantially radially from the helically-cut metal tube (11) and are oriented substantially parallel to the longitudinal axis (X'). Those of ordinary skill in the art will recognize, however, that the teeth need not be substantially parallel to the longitudinal axis (X') and that they may be arranged in other manners as well (e.g., a staggered configuration, a spiral configuration, or other configurations). The helical cut of the tube (11) imparts to each cutting tooth at least some motion independent of any other cutting tooth while the broach (10) moves proximally, distally, or rotationally. Because of the helical cut, the broach (10) is flexible in much the same way a spring is flexible (e.g., with regard to compression, torsion, and deviation from the broach section longitudinal axis). Consequently, at least a portion of said broach (10) can be displaced from (i.e., pulled or pushed away from) the broach longitudinal axis (X'), forming a displaced broach segment (14). When at least a portion of the broach (10) is displaced from the broach longitudinal axis (X') at the displaced broach segment (14), the displaced broach segment (14) forms, substantially, an arch. The arch comprises proximal and distal ends (15 & 16, respectively), a length therebetween, and a maximum height (wherein said maximum height is the length of a line between the broach longitudinal axis (X') and a point along the arch that is maximally displaced from the broach longitudinal axis (X'), wherein said line is perpendicular to the broach longitudinal axis).

Referring again to FIG. 1, the broach (10) is slidably positioned over a ramp wire (200). The ramp wire (200) comprises proximal and distal ends (210—encased by broach (10) in FIG. 1—and 220, respectively), and extreme distal end (230), which is anchored to the distal end (70) of the device (1). The ramp wire (200) is substantially enclosed by the broach (10), proximally, and is oriented substantially coaxially with broach longitudinal axis (X'). At least a portion of the ramp wire (200) is displaced from the broach longitudinal axis (X') at a displaced ramp wire segment (14'), the displaced ramp wire segment (14') forming, substantially, an arch. Because the ramp wire (200) is anchored to the distal end (70) of the device, the broach (10) is free to slide (i.e., axial translation and axial rotation) over the stationary ramp wire (200).

As shown in FIG. 1, at least at a portion of the broach proximal and distal ends (12 & 13, respectively), the broach (10) is attached to a drive rod (300). The drive rod (300) comprises proximal and distal attachment points (310 & 320, respectively) at which the drive rod (300) is connected to the broach (10). The cutting surfaces (20) are located between the proximal and distal attachment points (310 & 320, respectively), and the broach (10) is not connected to the drive rod (300) over the broach length lying between the proximal and distal attachment points (310 & 320, respectively). In other words, the broach comprises proximal and distal attachment points (310 & 320, respectively) and a length therebetween, at which attachment points (310 & 320) the broach is attached to the drive rod (300) and over which length the broach is not attached to the drive rod. The drive rod (300) is oriented substantially coaxially with broach longitudinal axis (X'). The broach (10) is connected to the drive rod proximal and distal attachment points (310 & 320, respectively) so as to enable the broach (10), slidably positioned over ramp wire (200), to slide over the displaced ramp wire segment (14') and form displaced broach segment (14). In other words, the broach (10) is flexed prior to attachment to the drive rod (300) proximal and distal attachment points (310 & 320, respectively) to allow contour motion (i.e., the formation of an arch (14) by the broach) of the broach (10) over the displaced ramp wire segment (14') of the ramp wire (200).

The broach (10), ramp wire (200), and drive rod (300) are attached at their proximal ends to the distal end (410) of drive tube (400). The drive tube (400) is flexible and possesses sufficient torsional rigidity to turn the broach and drive rod about the longitudinal axis (X). The drive tube (400) may be made of materials known to those of ordinary skill in the art (e.g., polyimide).

Referring now to FIGS. 2-6, the instant device (1) further comprises a longitudinal axis (X), a cylinder (30) having proximal and distal ends (40 & 50, respectively), device proximal and distal ends (60 & 70, respectively), and atraumatic tip (2). The cylinder (30) at least partially encloses the broach (10), ramp wire (200), and drive rod (300). The cylinder (30) further comprises a cylinder wall (80), a longitudinal axis (X") substantially coaxial with the longitudinal axis (X) of the instant device (1), and proximal and distal ends (40 & 50, respectively). The cylinder (30) further comprises a window (100) having a length (L) and a width (W), the length being oriented along the longitudinal axis of the cylinder (90) and the width oriented perpendicular to the window length. The cylinder (30) further comprises at least one fluid in-flow lumen (110) in fluid communication with the window (100), at least one fluid out-flow lumen (120) in fluid communication with the window (100), and a guide-wire lumen (130). The cylinder further comprises chamber (125) which is in fluid communication with the body lumen in which the device (1) is inserted, with the window (100), with the at least one fluid in-flow lumen (110), and with the at least one fluid out-flow lumen (120). The at least one fluid in-flow lumen (110) and the at least one fluid out-flow lumen (120) terminate at the chamber (125).

Figure 4:
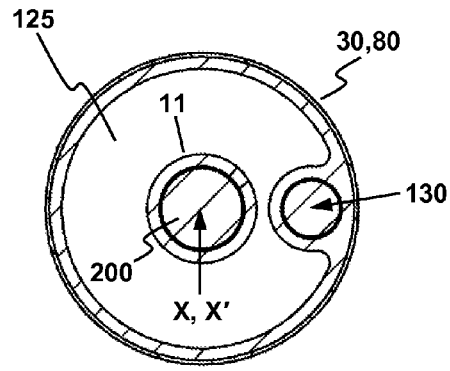
FIG. 4 is a cross-sectional view of a device of the present disclosure along plane B-B of FIG. 2.
Figure 5:
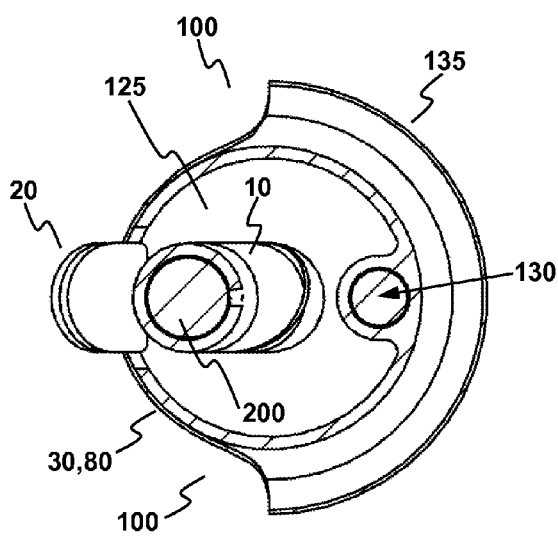
FIG. 5 is a cross-sectional view of a device of the present disclosure along plane C-C of FIG. 2.
Figure 6:
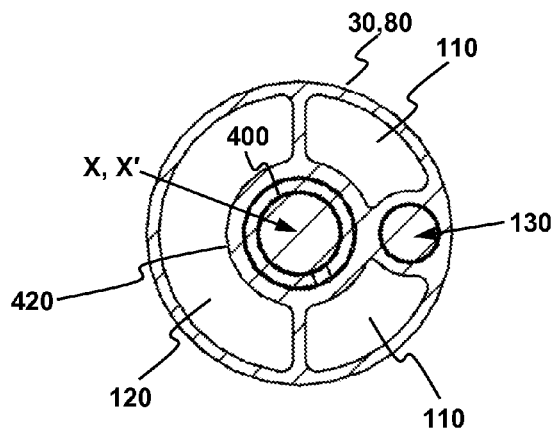
FIG. 6 is a cross-sectional view of a device of the present disclosure along plane D-D of FIG. 2.

As shown by FIG. 4, which is a cross-section of the device distal to the window (100), the ramp wire (200) and the helically-cut tube (11) of the broach (10) are substantially co-axial with the longitudinal axis (X) at the distal end of the device (1). As shown in FIGS. 4-6, the at least one fluid in-flow lumen (110), the at least one fluid out-flow lumen (120), and the guide-wire lumen (130) are oriented substantially longitudinally, along the longitudinal axis (X).

As shown in FIG. 5, which is a cross-section through the window (100), the broach (10) and ramp wire (200) are displaced from the longitudinal axis (X) at at least a portion of the broach (10) and ramp wire (200). For the sake of clarity, the drive rod (300) is not shown in FIG. 5, but it would lie substantially coaxial with the longitudinal axis (X). FIG. 5 also shows that the teeth (20) are exposed by the window (100).

As shown in FIG. 6, which is a cross-section of the device proximal to the window (100), the drive tube (400) lies within a drive tube lumen (420) which is substantially coaxial with the longitudinal axis (X). The drive tube lumen (420) is substantially surrounded by the at least one fluid inflow lumen (110), the at least one fluid outflow lumen (120), and the guide-wire lumen (130).

Figure 2:
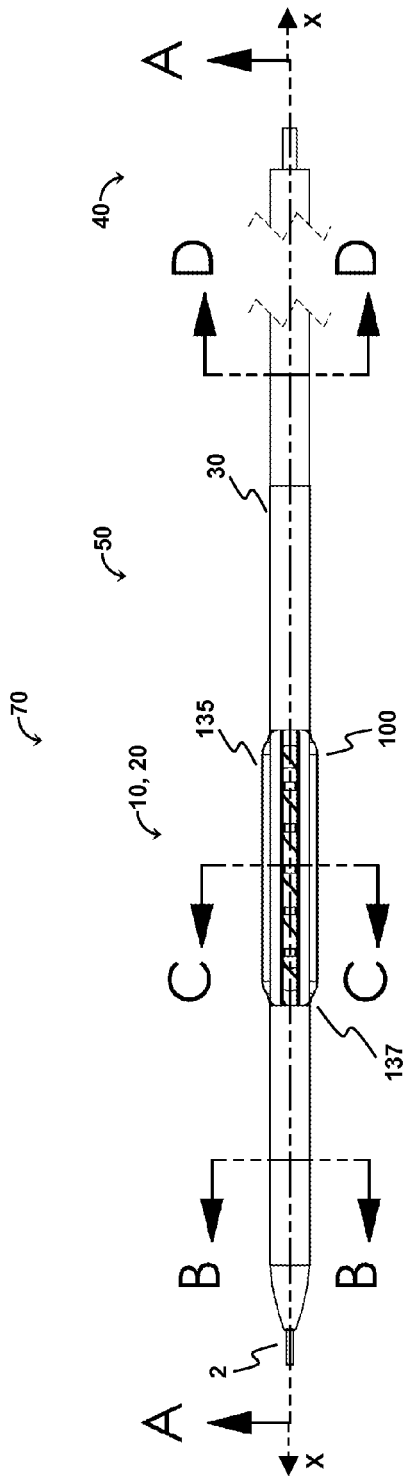
FIG. 2 shows the distal end of a device of the present disclosure.
Figure 3:
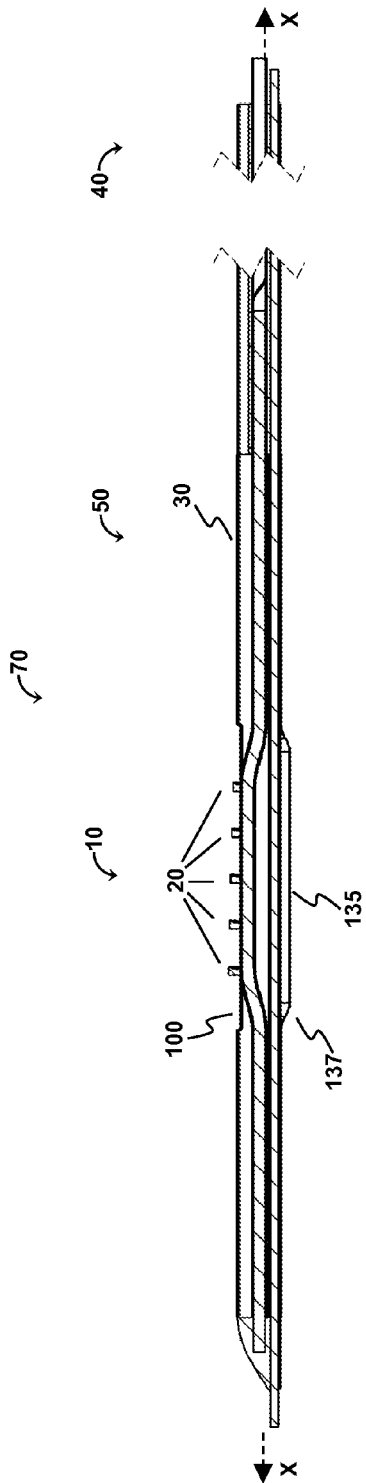
FIG. 3. shows a cutaway view of a device of the present disclosure along plane A-A (sagittal plane) of FIG. 2.

As shown most clearly in FIGS. 2, 3, and 5, the device (1) may further comprise an opposition sleeve (135). The opposition sleeve (135) is substantially cylindrical, and slidably envelops at least a portion of the cylinder (30). The opposition sleeve (135) has proximal and distal ends (136 and 137, respectively) such that the proximal end is operationally engaged with opposition sleeve control (630), shown in FIG. 9. The distal end (137) of opposition sleeve (135) is attached to the cylinder (30) at least at a point or band opposite the window (100). The distal end (137) of opposition sleeve (135) comprises at least one longitudinal slit substantially opposite the window (100). By engaging the opposition sleeve control (630), the opposition sleeve (135) slides along the cylinder (30) in a proximal-to-distal direction. Because the distal end (137) of opposition sleeve (135) is attached to the cylinder (30) at least at a point or band opposite the window (100), and because the distal end (137) of opposition sleeve (135) comprises at least one longitudinal slit substantially opposite the window (100), engaging the opposition sleeve control (630) causes the distal end (137) of the opposition sleeve (135) to bend, flex, or bulge away from the cylinder (30) along the at least one slit. The result is that the distal end (137) of the opposition sleeve (135) will push against the inner wall of the body lumen in which the device (1) is inserted, thereby pushing the window (100), broach (10), and teeth (20) toward the opposite side of the same inner wall. In this way, the device (1) may contact a lesion or plaque to allow the teeth (20) to more effectively remove the lesion or plaque.

In one embodiment, the instant device is operated to progressively enlarge and to make round or patent a body lumen (e.g., a blood vessel, thereby reversing plaque accumulation and restoring vascular flow) in whatever area is clinically relevant for the patient.

In one embodiment, fluid (e.g., physiologic saline, contrast fluid, pharmaceutical or biological therapeutics in suspension or solution, etc.) may be introduced to the body lumen being treated with the instant device via the at least one fluid in-flow lumen in communication with the window. Any fluid introduced, as well as blood, other bodily fluids, and material removed via action of the broach, may be removed from the body lumen being treated with the instant device via the at least one fluid out-flow lumen in fluid communication with the window.

Figure 7:
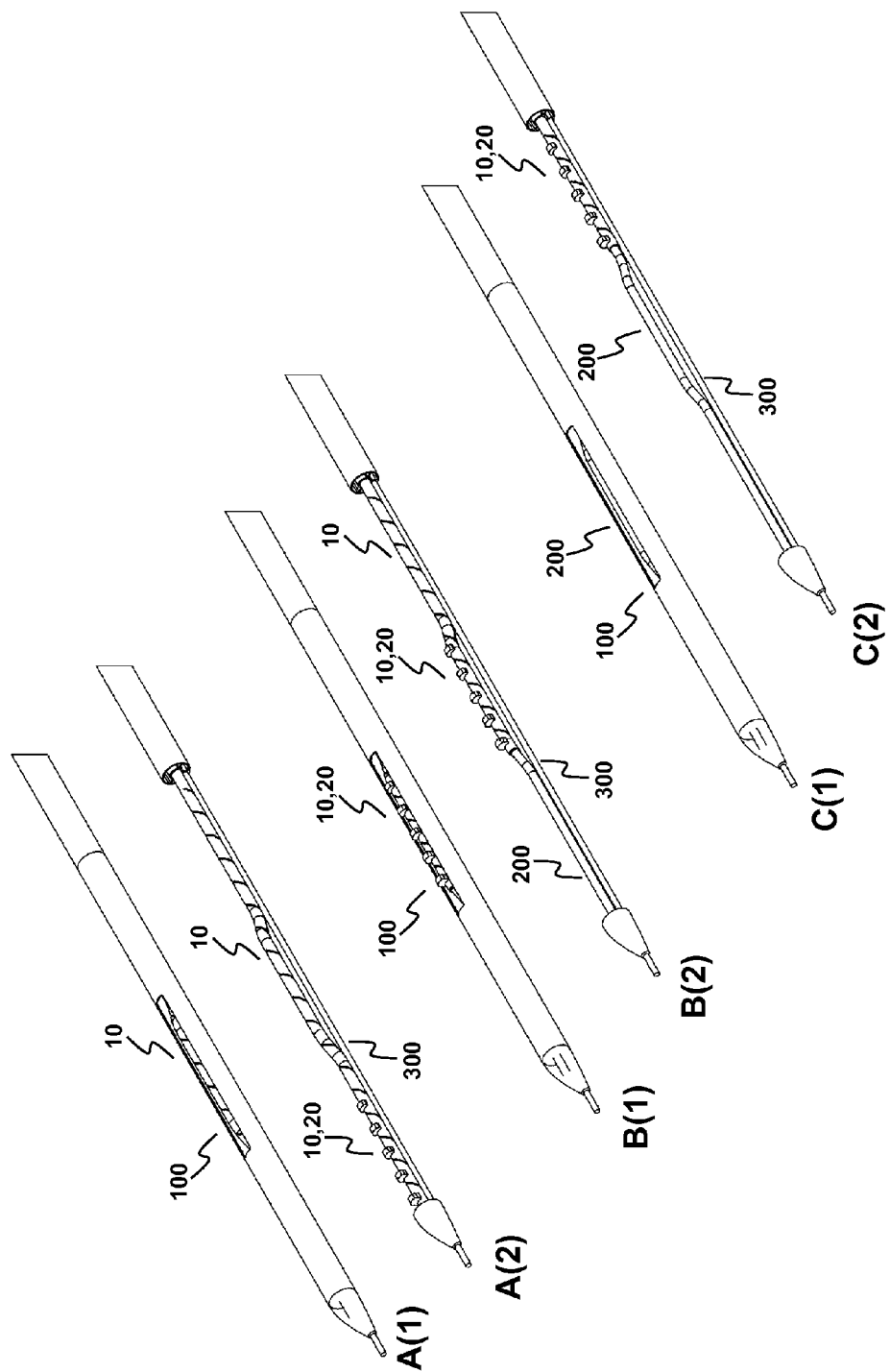
FIG. 7 shows the movement of the broach and drive rod of the present disclosure in a device of the present disclosure.
Figure 8:
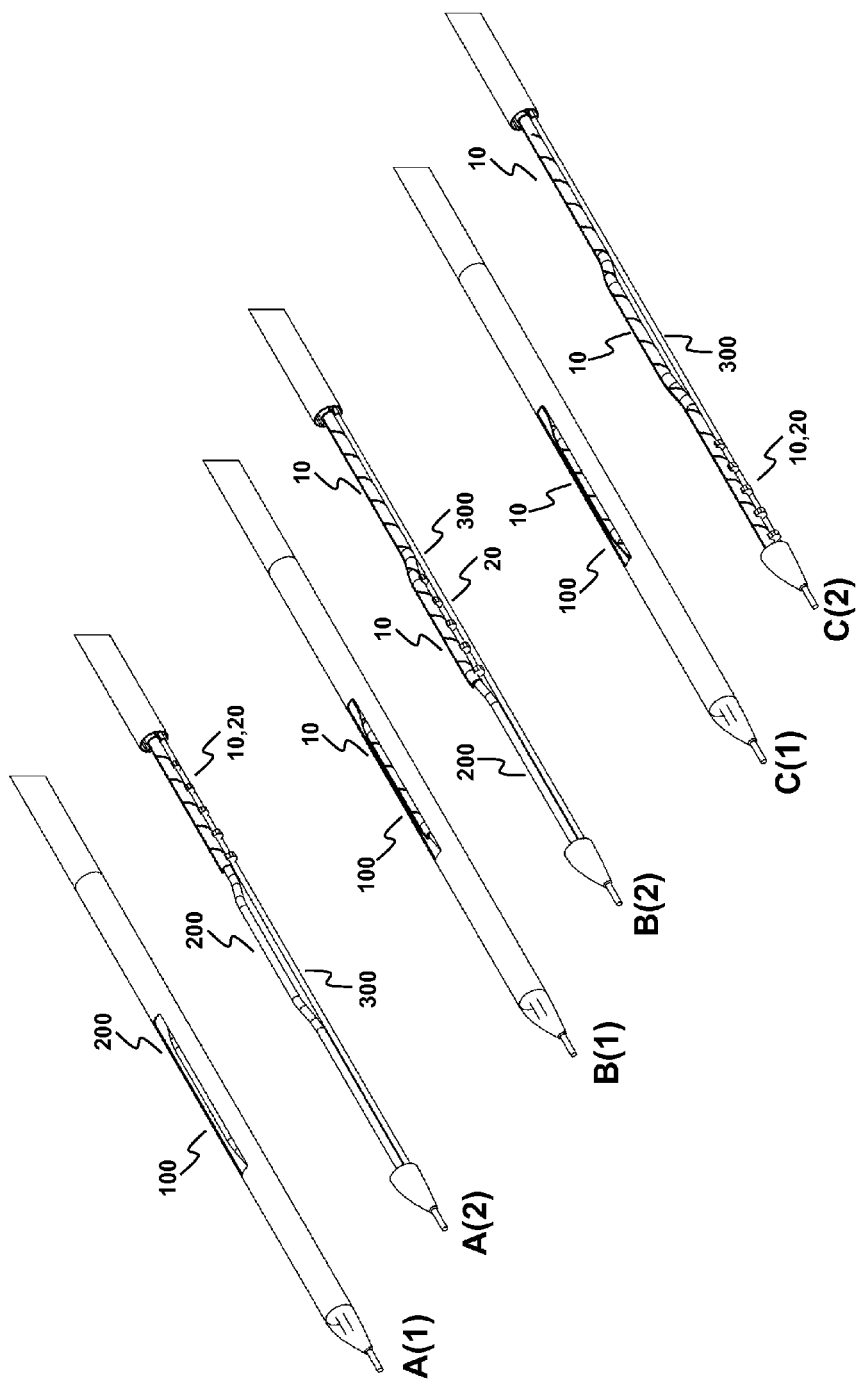
FIG. 8 shows the movement of the broach and drive rod of the present disclosure in a device of the present disclosure.

During operation of the device (1), the cutting surfaces (20) of the broach (10) are alternately exposed via cylinder window (100) and occluded via the cylinder (30) as shown in FIGS. 7A(1) through 8C(2). In one embodiment, the broach may move linearly along the longitudinal axis of the instant device in a first longitudinal direction (e.g., as shown by the relative position of the broach (10) and teeth (20) in FIGS. 7A(1) through 7C(2)). Then, upon reaching a first pre-determined position, as shown in FIGS. 7C(1) and (2), the broach rotates (e.g., as shown by comparison between FIGS. 7C(1) and (2) versus FIGS. 8A(1) and (2)) about the longitudinal axis in a first axial direction until it reaches a second pre-determined position (e.g., as shown in FIGS. 8A(1) and (2)). From the second pre-determined position, the broach again moves linearly along the longitudinal axis in a second longitudinal direction (e.g., as shown by the relative position of the broach (10) and teeth (20) in FIGS. 8A(1) through 8C(2)), wherein the first and second longitudinal directions are opposite directions along the longitudinal axis, until the broach reaches a third pre-determined position (e.g., as shown in FIGS. 8C(1) and 8C(2)). From the third pre-determined position, the broach rotates about the longitudinal axis in a second axial direction (e.g., as shown by comparison between FIGS. 8C(1) and (2) versus FIGS. 7A(1) and (2)), wherein the first and second axial directions are opposite directions about the longitudinal axis, until the broach reaches a fourth pre-determined position (e.g., as shown in FIGS. 7A(1) and 7A(2)). From the fourth pre-determined position, the broach may again travel linearly along the longitudinal axis in the first longitudinal direction until it again reaches the first pre-determined position. By moving repetitively through the first, second, third, and fourth pre-determined positions, the broach travels one circuit, which circuit may be repeated any number of times at the end-user's discretion. Persons having ordinary skill in the art will appreciate that the broach may start or stop at any of the aforementioned points or positions (or any position in between), that the fourth pre-determined position and the starting point may be substantially the same points, or they may be different (e.g., the starting point may be a "safety" position), and will appreciate further that the number of circuits traveled by the broach may be varied at the end user's discretion.

In one embodiment, similar to that depicted in FIGS. 7A(1) through 8C(2), the broach may begin at a starting point and move linearly along the longitudinal axis of the instant device in a first longitudinal direction. Then, upon reaching a first pre-determined position, the broach rotates about the longitudinal axis in a first axial direction until it reaches a second pre-determined position. Then, the broach again moves linearly along the longitudinal axis in a second longitudinal direction, wherein the first and second longitudinal directions are opposite directions along the longitudinal axis, until it reaches a third pre-determined position. Finally, the broach rotates further about the longitudinal axis further in the first axial direction, until it reaches a fourth pre-determined position (i.e., in this embodiment there is no second axial direction of rotation). From the fourth pre-determined position, the broach may again travel linearly along the longitudinal axis in the first longitudinal direction until it again reaches the first pre-determined position. By moving through the first, second, third, and fourth pre-determined positions, the broach travels one circuit, which circuit may be repeated any number of times at the end-user's discretion. Again, persons having ordinary skill in the art will appreciate that the broach may start or stop at any of the aforementioned points or positions (or any position in between), that the fourth pre-determined position and the starting point may be substantially the same points, or they may be different (e.g., the starting point may be a "safety" position), and will appreciate further that the number of circuits traveled by the broach may be varied at the end user's discretion.

The at least one fluid inflow lumen (110) has at least one distal terminus situated such that fluid expelled by the at least one fluid inflow lumen (110) flows over the teeth (20) of broach (10) while said teeth (20) are at about the most proximal position as the broach (10) travels a circuit. This fluid flow helps to clean the teeth (20) and flush particulate matter from the broach (10), generally. Similarly, the at least one fluid outflow lumen (120) has at least one distal terminus situated such that fluid expelled by the at least one fluid inflow lumen (110), fluid and particulate matter from the body lumen in which the device (1) is inserted, and particulate matter removed from the teeth (20) of broach (10) by the fluid action of fluid inflow lumen (110) is aspirated via said at least one fluid outflow lumen (120). The distal terminus of the at least one fluid outflow lumen (120) may be at about the most proximal position the teeth (20) may be found in as the broach (10) travels a circuit.

Optionally, a comb (not shown) or brush (not shown) or similar means may be attached to the inside of the cylinder (30) to facilitate the removal of debris from the teeth (20) of broach (10). Such comb, brush, or similar means may inter-digitate with the teeth (20) as the broach (10) rotates axially (e.g., in a first and/or second axial direction).

The amount of material (e.g., atherosclerotic plaque) removed by each cutting tooth may vary with the material being cut and with the depth of each cutting tooth. For discussion purposes, a cutting tooth designed to cut steel might remove only 0.0025" per tooth, while a cutting tooth designed to cut softer materials might remove 0.004" per tooth or more. The amount of atherosclerotic plaque cut by each cutting tooth is yet to be determined. Movement of the succession of teeth of the instant device removes the total amount of material determined for a single pass; the total amount to be removed per procedure is determined by the number of passes prescribed by the end-user.

The instant device is designed to be delivered over-the-wire (over a guide wire) so that the cylinder window through which the cutting teeth are exposed may be more easily positioned in a clinically relevant area in the occluded body lumen. Ease and certainty of placement facilitates plaque removal and assists restoration of the lumen diameter to provide adequate flow to the limbs or other target area.

In one embodiment, the arch (14, 14') is completely contained within the helically-cut broach section. In one embodiment, each tooth tip is hardened and ground to form a cutting edge optimized to cut arteriosclerotic plaque.

Figure 9:
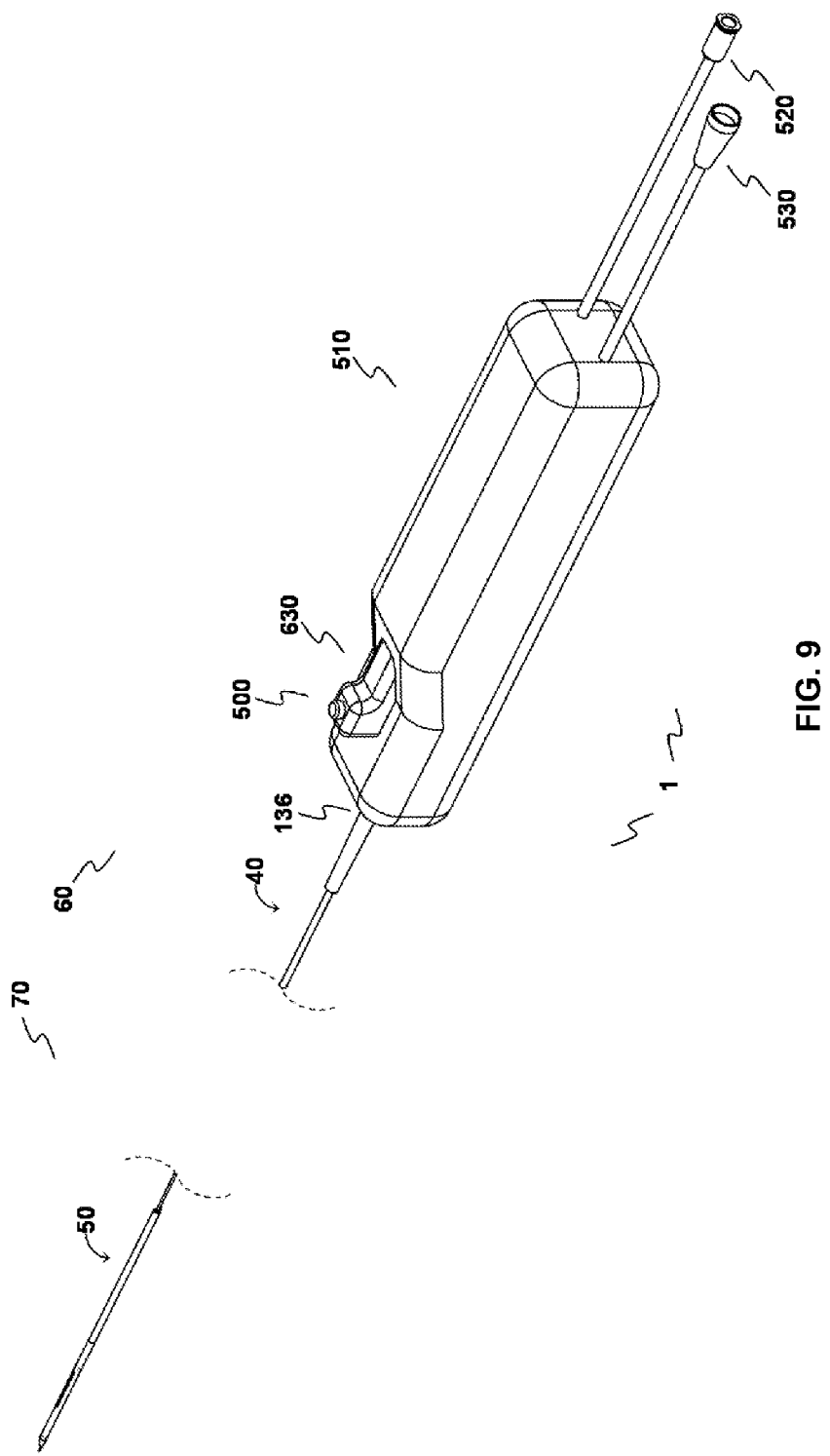
FIG. 9 shows a device of the present disclosure.
Figure 10:
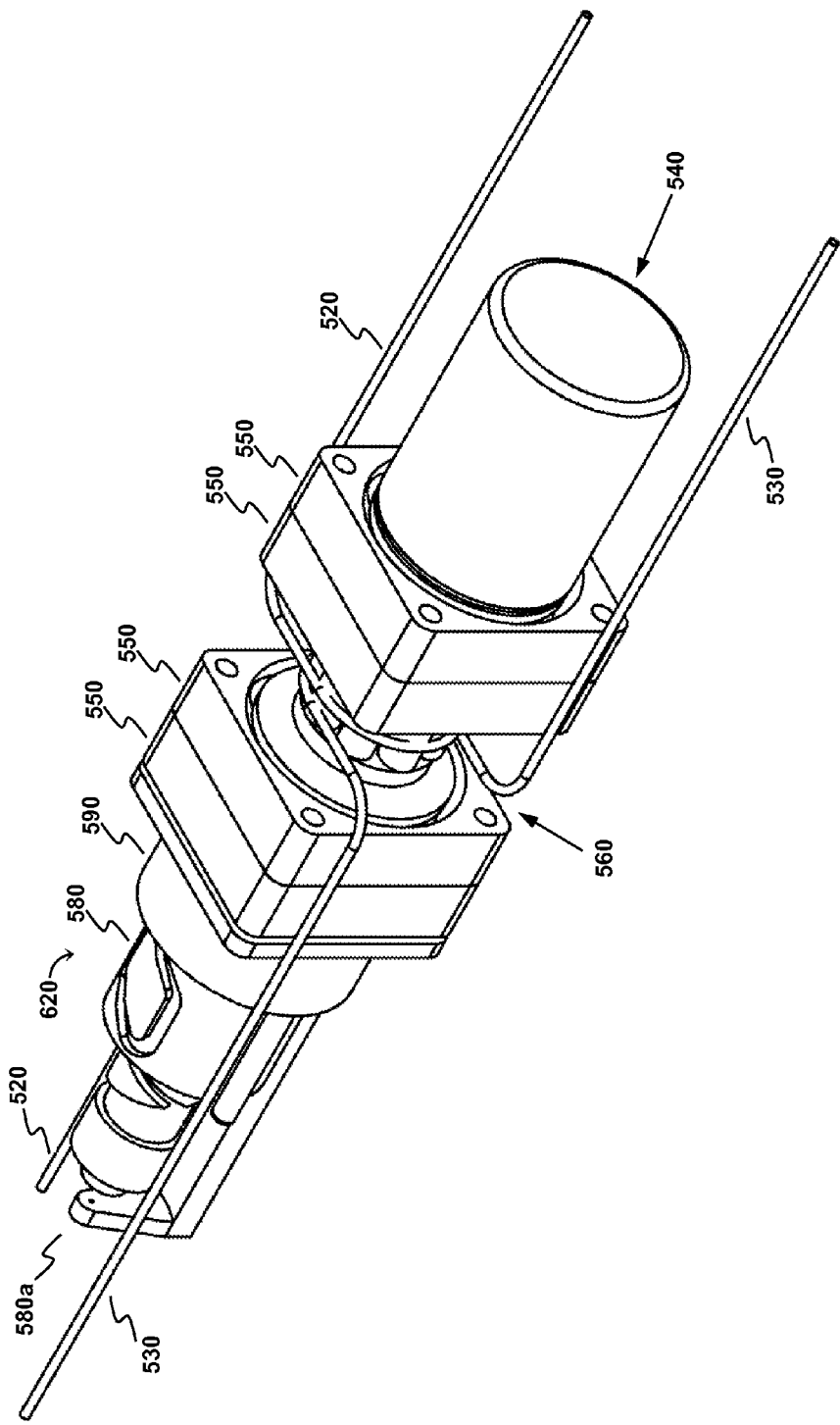
FIG. 10 shows the cutter drive assembly, peristaltic pump assembly, planetary gear packs, and drive motor contained within the hand piece of a device of the present disclosure.
Figure 11:
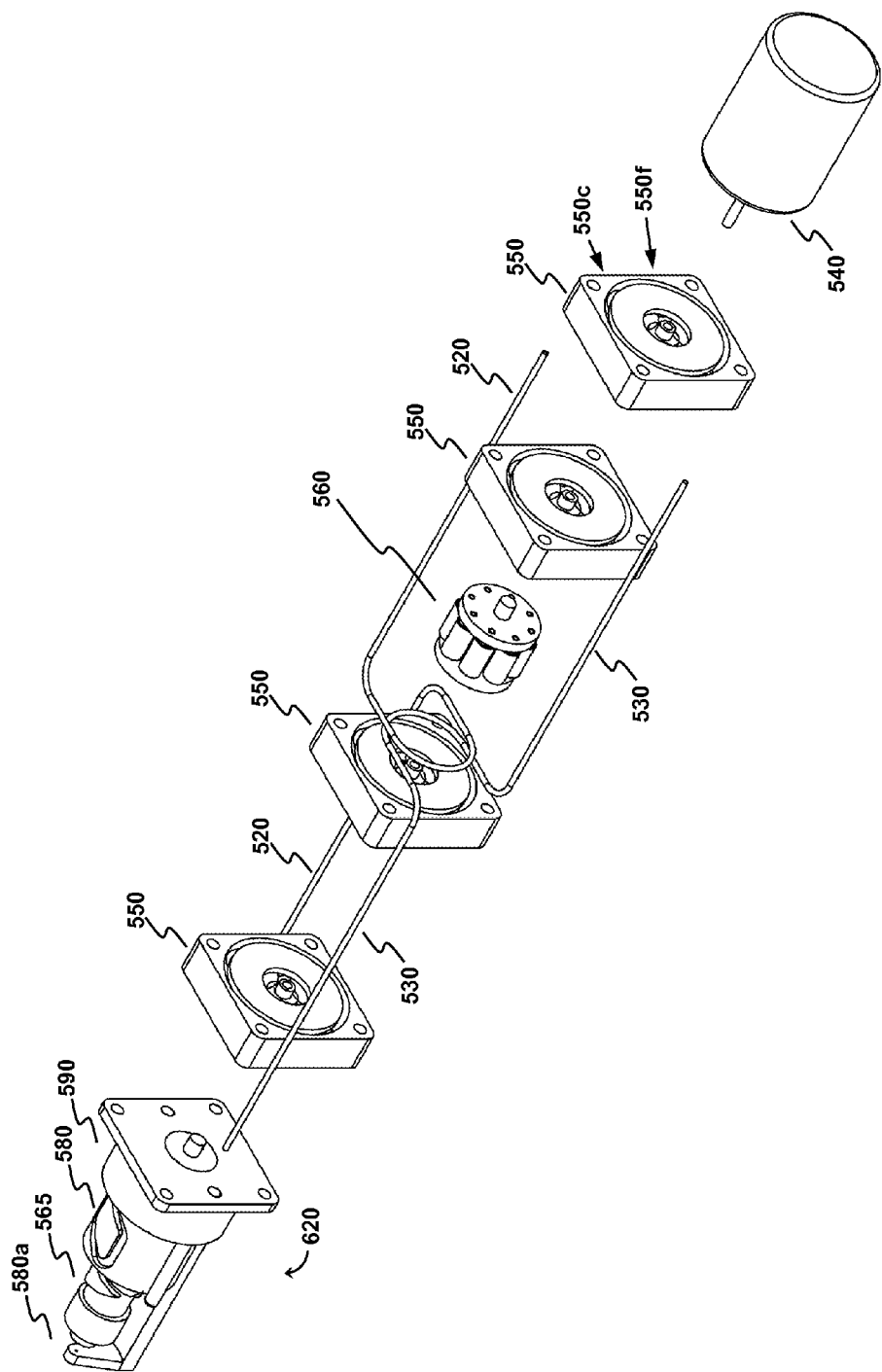
FIG. 11 is an exploded view of the cutter drive assembly, peristaltic pump assembly, planetary gear packs, and drive motor contained within the hand piece of a device of the present disclosure.
Figure 13A:
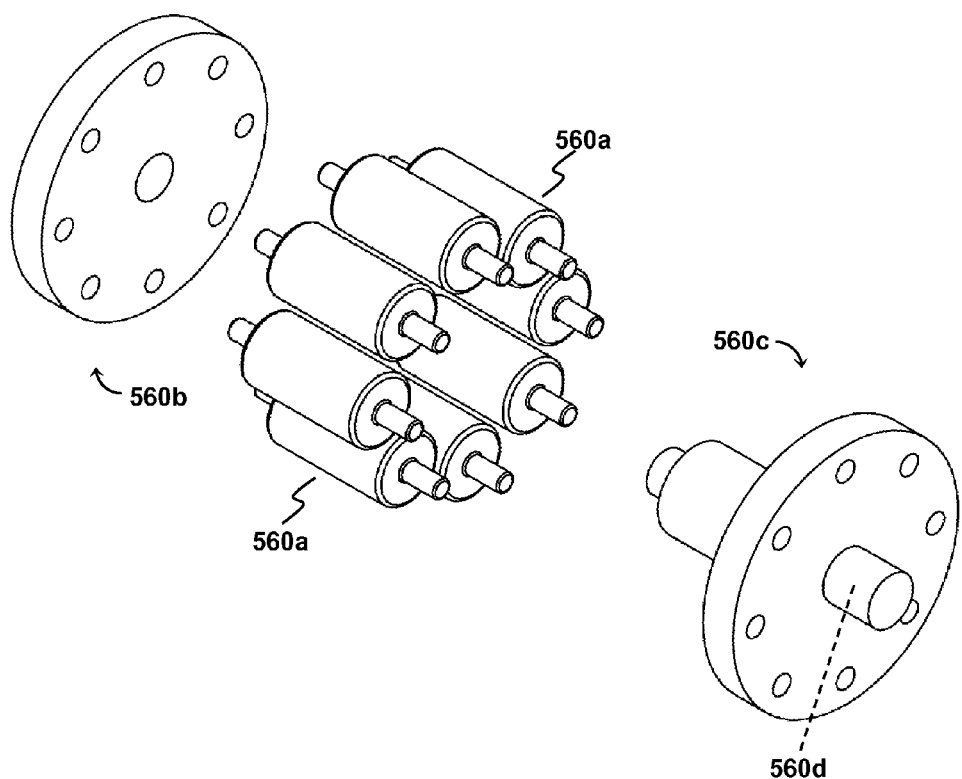
FIG. 13A is an exploded view of the peristaltic pump assembly.
Figure 13B:
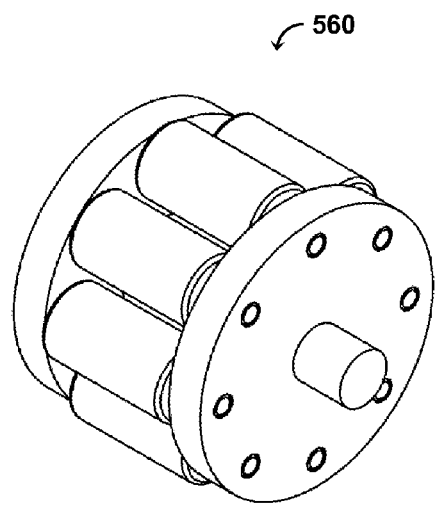
FIG. 13B shows the assembled peristaltic pump assembly.

Once the distal catheter portion (70) of the device (1) is in the desired position, the device (1) is activated via a switch (500) on a hand piece (510), as shown at FIG. 9. The hand piece (510) comprises a motorized drive and two-way pump system, described below and shown at FIGS. 10-14. The hand piece (510) drives the helically-cut broach (10) of the device (1) to continuously remove plaque. This action is sequential, and occurs in the following order: 1) the broach tooth "train" translates axially distal to proximal, riding up the ramp wire (200) to allow the teeth (20) to exit out of the aperture or window (100) in the catheter (30) and engage the plaque, making progressively larger cuts into the lesion as it moves along the ramp wire (200); 2) at the end of the distal to proximal axial stroke, the broach tooth "train" rotates about 90 to about 180 degrees through a comb feature (not shown) and/or a fluid flush stream to remove and flush the plaque debris from the teeth, and move the debris proximally through the fluid outflow lumen (120) of the catheter (30) to a waste container via the continuous flushing action provided by the hand piece (510, 520, 530); 3) the broach tooth "train" then moves axially, proximal-to-distal along the ramp wire (200), but since the cutting teeth (20) have been rotated about 90 to about 180 degrees, there is no cutting action at this step; 4) once at the distal position, the broach tooth "train" is rotated back to the "home" position and the cycle begins again, allowing the user to remove the amount of plaque necessary to restore adequate blood flow. As will be appreciated by those of ordinary skill in the relevant arts, the rotations of the broach tooth "train" need not be exactly 90 or 180 degrees, but one of the rotations must be of sufficient degree that the broach tooth "train" is "hidden" by the catheter (30) as the "train" moves proximal-to-distal along the ramp wire (200), while the other rotation is of sufficient degree to re-orient the "train" so that the "train" may exit the window (100) as the "train" moves distal-to-proximal along the ramp wire (200).

The hand piece (510) contains a battery-operated motor (540) that drives a series of planetary gear packs (550), shown in FIGS. 12A-C, allowing for different rotational speeds at different sections of the drive within the hand piece (510) to accomplish different functions. The planetary gear packs (550) further comprise gear pack frame (550a), gear pack cover (550b), planetary gears (550c), sun gear (550d), and gear pack back (550e). As shown in FIGS. 12B and 12C, the planetary gear packs (550) further comprise a drive input (550f) and drive output (550g).

The first stage of the drive reduction drives the infusion and aspiration pumps (560). These pumps (560, 520, 530) are peristaltic tubing pumps driven by a series of rollers (560*a*) within the hand piece (510), and operate at the first stage of the gear reduction (550*a*). The pumps (560) further comprise a pump end plate (560*b*), a pump drive plate (560*c*), and a drive input (560*d*).

The second stage of the gear reduction drives the linear motion (i.e., axial translation) of the tooth train. In order to maintain continuous pumping action and share a common drive, the change in linear direction (i.e., distal-proximal & proximal-distal strokes) is controlled by a secondary mechanism instead of by reversing the drive motor. This is accomplished by using an adaptation of a "double screw of Napier" shaft or reversing drive cam—a shaft that has two helical groves of equal pitch in opposite directions timed at 180 degrees (565). A follower (570) rides along a first groove (565*a*) of the reversing drive cam (565), moving in one helical direction until it reaches the end of the groove, where it dwells until it engages a second, opposite direction groove (565*b*), and returns in the opposite direction. A common example of this action would be what fishermen refer to as a "level-winding reel".

The about 90 to about 180 degree rotation of the tooth train at each end of each stroke is accomplished by using a simple drum cam (580) incorporated into the proximal portion of the drive tube (400) at a distal portion (580*a*) of the drum cam (580). Consequently, the rotation of the tooth train with respect to its position with the aperture or window (100) is coordinated properly during the stroke described above. The reversing drive cam (565) further comprises a drive input (565*c*), and is engaged with the drum cam (580) via cutter cam drive bearing (590). The cutter cam drive bearing is attached to guide frame (600) via cutter cam drive bearing guide pins (610). Together, the reversing drive cam (565), cutter cam bearing (590), reversing cam follower (570), cutter path drum cam (580), guide frame (600), and cutter cam drive bearing guide pins (610) comprise the cutter drive assembly (620).

The following examples of use are not intended to be an exhaustive list, as those familiar in the art will know many more sub-categories of treatment that keep within the spirit of the disclosure of the device and the method.

EXAMPLE 1

Access to the treatment site would be first initiated by placing a vascular guide wire using standard, minimally invasive vascular techniques (i.e. "Seldinger technique"). The device of the present disclosure would be delivered along this wire in what is called "over the wire". It is important to note that this device can either be designed for "rapid exchange" or "monorail" delivery (only the distal portion of the device tracks over the guide wire) or traditional over the wire delivery (the entire length of the device tracks over the guide wire).

A portion of the device of the present disclosure would be delivered to the treatment site and positioned with the aide of contrast injections and other radiologic tools and imaging devices. In the event the treatment region is longer than the aperture of the device of the present disclosure, treatment would be carried out in linear and/or rotational segments to ensure uniform plaque removal around the inside diameter of the body lumen, over the length of the entire lesion.

A sterile fluid supply (e.g. a liter bag of saline optionally mixed with an appropriate amount of contrast media) may be connected to the inlet port of the hand piece of the device of the present disclosure. A drain line would be connected to the exit port of the hand piece of the device of the present disclosure and connected to a suitable collection container that allows collection of the excised plaque for analysis, if desired.

The distal catheter portion would be threaded over the proximal end of the guide wire (already in place), and slid through the guide sheath to the operative site. The physician would push the opposition sleeve control (630) forward to deploy the opposition sleeve (135), which positions the cutter aperture against the plaque to be excised. The physician would press and hold the cycle start switch (500), which begins the plaque excision (cyclical broaching action). Plaque is removed and may be monitored by radiographical imaging in real time. Releasing the cycle start switch (500) would stop the broaching action at the end of its cycle, and allow the physician to reposition the device of the present disclosure circumferentially or axially to maximize the amount of plaque removed and ensure uniform removal.

Once the lesion is treated to the satisfaction of the physician, the device may then be repositioned in a different section of the body lumen to continue treatment (i.e., in the event that there are multiple lesions) by repeating the above procedures.

All references cited in this specification are herein incorporated by reference as though each reference was specifically and individually indicated to be incorporated by reference. The citation of any reference is for its disclosure prior to the filing date and should not be construed as an admission that the present disclosure is not entitled to antedate such reference by virtue of prior invention.

It will be understood that each of the elements described above, or two or more together may also find a useful application in other types of methods differing from the type described above. Without further analysis, the foregoing will so fully reveal the gist of the present disclosure that others can, by applying current knowledge, readily adapt it for various applications without omitting features that, from the standpoint of prior art, fairly constitute essential characteristics of the generic or specific aspects of this disclosure set forth in the appended claims. The foregoing embodiments are presented by way of example only; the scope of the present disclosure is to be limited only by the following claims.

We claim:
1. A device comprising:
   a) a longitudinal axis;
   b) a broach comprising cutting teeth, said broach substantially coaxial with the longitudinal axis and said cutting teeth projecting substantially radially from said longitudinal axis;
   c) a ramp wire substantially coaxial with the longitudinal axis, wherein at least a portion of said ramp wire is displaced from said longitudinal axis;
   d) a drive rod substantially coaxial with the longitudinal axis; and
   e) a reversing drive cam;
   wherein at least a portion of the ramp wire is slidably enclosed by the broach along a ramp wire length,
   wherein said reversing drive cam causes
   i) distal-to-proximal axial translation of the broach over the ramp wire, followed by
   ii) about 90 to about 180 degrees of axial rotation of the broach around the ramp wire, followed by
   iii) proximal-to-distal axial translation of the broach over the ramp wire, followed by
   iv) about 90 to about 180 degrees of axial rotation to the broach around the ramp wire; and followed by
   v) optional repetition of steps (i) through (iv).

2. The device of claim 1, wherein said broach comprises a helically-cut tube, and wherein said ramp wire is anchored to a distal end of the device.

3. The device of claim 2, wherein said broach comprises proximal and distal attachment points and a length therebetween, at which attachment points the broach is attached to the drive rod and over which length the broach is not attached to the drive rod.

4. The device of claim 3, wherein said length is sufficient to accommodate the displacement of the ramp wire from the longitudinal axis.

5. The device of claim 3, further comprising a cylinder, wherein said cylinder:
   a) is substantially coaxial with the longitudinal axis;
   b) at least partially encloses the broach, ramp wire, and drive rod; and
   c) further comprises a window, said window exposing at least a portion of said broach, ramp wire, and drive rod.

6. The device of claim 5, wherein said cylinder further comprises:
   a) at least one fluid in-flow lumen in fluid communication with said window;
   b) at least one fluid out-flow lumen in fluid communication with said window;
   c) a guide-wire lumen; and
   d) a chamber in fluid communication with said window, said fluid in-flow and out-flow lumens, and said guide-wire lumen.

7. The device of claim 6, further comprising an opposition sleeve.

8. The device of claim 6, further comprising at least one planetary gear pack, an infusion pump, and an aspiration pump.

9. A method for modifying a body lumen of a mammal in need thereof, the method comprising:
   a) inserting the device of claim 1 into said body lumen; and
   b) operating said reversing drive cam, thereby causing;
      i) distal-to-proximal axial translation of the broach over the ramp wire, followed by
      ii) about 90 to about 180 degrees of axial rotation of the broach around the ramp wire, followed by
      iii) proximal-to-distal axial translation of the broach over the ramp wire, followed by
      iv) about 90 to about 180 degrees of axial rotation to the broach around the ramp wire; and followed by
      v) optional repetition of steps (i) through (iv).

10. The method of claim 9, wherein said device further comprises a cylinder, wherein said cylinder:
   a) is substantially coaxial with the longitudinal axis;
   b) at least partially encloses the broach, ramp wire, and drive rod; and
   wherein said cylinder further comprises:
   c) a window, said window exposing at least a portion of said broach, ramp wire, and drive rod;
   d) at least one fluid in-flow lumen in fluid communication with said window;
   e) at least one fluid out-flow lumen in fluid communication with said window;
   f) a guide-wire lumen; and
   g) a chamber in fluid communication with said window, said fluid in-flow and out-flow lumens, and said guide-wire lumen.

11. The method of claim 10, wherein said modifying comprises removing plaque from said body lumen.

12. The method of claim 10, wherein said modifying comprises enlarging, making round, or making patent said body lumen.

\* \* \* \* \*